United States Patent [19]

Rubino et al.

[11] 4,028,390

[45] June 7, 1977

[54] METHODS OF MAKING BASIC ZIRCONIUM COMPLEXES

[75] Inventors: Andrew M. Rubino, New Providence; John L. Jones, Watchung; Edward S. Bretschneider, Plainfield, all of N.J.

[73] Assignee: Armour Pharmaceutical Company, Phoenix, Ariz.

[22] Filed: Mar. 26, 1975

[21] Appl. No.: 562,300

[52] U.S. Cl. .............................. 260/429.3; 424/66
[51] Int. Cl.$^2$ ......................................... C07F 7/00
[58] Field of Search .................. 260/448 R, 429.3; 424/68, 66, 65, 47

[56] References Cited

UNITED STATES PATENTS

| | | |
|---|---|---|
| 2,236,387 | 3/1941 | Wallace et al. ................. 424/68 |
| 2,814,584 | 11/1957 | Daley ............................. 424/66 |
| 2,814,585 | 11/1957 | Daley ............................. 424/66 |
| 2,854,382 | 9/1958 | Grad .............................. 424/68 |
| 3,407,254 | 10/1968 | Siegal et al. ..................... 424/66 |
| 3,792,068 | 2/1974 | Luedders et al. .............. 424/47 X |

*Primary Examiner*—Helen M. S. Sneed
*Attorney, Agent, or Firm*—Frank T. Barber; William W. Schwarze

[57] ABSTRACT

Basic zirconium gels may be used to form complexes with conventional aluminum and/or zirconium antiperspirant systems. The freshly prepared basic zirconium gels provide both a buffer for the highly acidic aluminum-zirconium complexes and an additional source of zirconium as an active ingredient in the antiperspirant. The preferred basic zirconium gels are basic zirconium-amino acid compounds, particularly basic zirconium glycinates, and the compounds are preferably added to aluminum-zirconium systems in the form of a wet gel. The preferred basic zirconium glycinate is formed by first reacting sodium carbonate with glycine, and then reacting the resulting sodium glycinate with a zirconium oxy or zirconium hydroxy compound to precipitate out the zirconium basic glycinate gel. The various complexes of the invention may be used in conventional antiperspirant forms, including aqueous solutions, aerosol sprays, powder-in-oil aerosol sprays, creams, lotions, cream sticks, etc.

14 Claims, No Drawings

METHODS OF MAKING BASIC ZIRCONIUM COMPLEXES

BACKGROUND OF THE INVENTION

The present invention relates to basic zirconium complexes and methods of making and using the same in antiperspirants. More particularly, the invention is directed to the production and use of basic zirconium carbonates and basic zirconium-amino acid compounds in highly acidic aluminum and/or zirconium antiperspirant systems.

It has been known in the art for some time that zirconium salts provide exceptionally effective antiperspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an antiperspirant has a pH of only about 0.8 and a solution of zirconyl hydroxy chloride which is effective as an antiperspirant has a pH of only about 1.2. As a result, it is necessary to buffer these solutions up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an antiperspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and 2,854,382 to Grad) or aluminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

In addition, Rubino copending application Ser. No. 418,712, filed Nov. 23, 1973, entitled "Aluminum-Zirconium Anti-Perspirant Systems With Salts Of Amino Acids", and other related copending applications describe other systems in which amino acids have been incorporated in aluminum-zirconium complexes to offset the acidity of the zirconium and aluminum as well as provide other advantages to the antiperspirant. Nevertheless, still more efficient and advantageous methods are being sought to combat the acidity of aluminum and/or zirconium while at the same time maintaining or improving antiperspirant efficacy.

BRIEF SUMMARY OF THE INVENTION

According to the present invention, astrigent complexes useful as antiperspirant ingredients are formed by reacting acidic aluminum and/or zirconium compounds with a freshly prepared basic zirconium compound selected from basic zirconium-amino acid gels, zirconium hydroxide gels, basic zirconium carbonate gels and mixtures thereof, to form a complex having an Al/Zr mol ratio of about 10:1 to 1:10, and preferably about 3:1 to 1:6. When dissolved in an aqueous solution to the extent of about 5 to 20 weight percent (solids basis), the complexes will produce a solution pH of at least about 3, and preferably in the range of about 3 to 5. The complexes may be dried to a powder form and used in any of a wide variety of conventional antiperspirant forms, including lotions, creams, roll-ons, aerosol sprays, and powder-in-oil aerosol sprays.

The basic zirconium carbonates are preferably reacted with acidic aluminum halides, such as aluminum chloride ($AlCl_3$), or lower basic aluminum halides to form complexes having an Al/Zr mole ratio of about 4:1 to 1:4 and preferably about 2:1 to 1:2. Such complexes should also have a corresponding solution pH of about 3 to 5, and may be used in various antiperspirant forms.

The present invention further includes an improved method for preparing basic zirconium-amino acid gels especially for use in forming the complexes of the present invention. According to the improved method, the basic zirconium-amino acid gel is prepared by reacting in aqueous medium a water soluble salt of an amino acid and a water soluble zirconium salt to precipitate the basic zirconium gel. Preferably, the water soluble amino acid salt is prepared by reacting the amino acid with an alkali metal or ammonium carbonate or bicarbonate. The basic zirconium-amino acid gel is preferably used in its wet form when preparing the antiperspirant complexes of the present invention.

DETAILED DESCRIPTION OF PREFERRED EMBODIMENTS

The astrigent or acid aluminum compounds useful in forming the antiperspirant complexes of the present invention include aluminum halides, preferably aluminum chloride ($AlCl_3$), and basic aluminum compounds and complexes which are known in the antiperspirant art for their cationicity and antiperspirant effectiveness and other properties. Aluminum chloride has been known for many years as one of the most effective antiperspirant compositions available. However, the use of aluminum chloride alone has been necessarily limited, due to the extreme acidity of even weak aluminum chloride solutions.

However, when complexed with the basic zirconium compounds according to the present invention, aluminum chloride is buffered to yield effective antiperspirant solutions having an acceptable pH of at least about 3. That is, when aluminum chloride is reacted with either basic zirconium-amino acid compounds or basic zirconium carbonates, complexes are formed which have a suitable buffered acidity as well as containing zirconium as an additional antiperspirant ingredient.

The basic aluminum compounds which may be used in forming the complexes of the present invention include many of the conventional basic aluminum salts which have been known to the antiperspirant art for some time, and which have a degree of antiperspirant efficacy in their own right, as a result of the presence of the active aluminum ion. These basic aluminum salts may be represented by the following general empirical formula:

wherein x may vary from greater than 0 to less than 6, 6-nx is greater than or equal to 0, n is the valence of A, and A is selected from the group consisting of halide, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the one-third to two-thirds basic aluminum chlorides (also referred to as lower basic aluminum chlorides), in which A is chloride and x is between about 2 and 4 and need not be an integer. Thus, such basic aluminum chlorides may be represented by the formulas

$Al_2(OH)_2Cl_4$ and $Al_2(OH)_4Cl_2$

The basic aluminum chlorides are also referred to as aluminum chlorhydroxide or aluminum chlorhydrate or aluminum hydroxy chloride, and are readily available in the art.

In addition to the simple basic aluminum salts indicated above, complexes or derivatives of the basic aluminum slats may also be used advantageously in the complexes of the present invention. Examples of such derivatives or complexes include the phenolsulfonate derivatives described in U.S. Pat. No. 3,634,480 to Sheffield. Such complexes are formed by reacting 5/6 basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present specification.

Of course, it should be understood that not all possible combinations of aluminum chloride and basic aluminum compounds will work in accordance with the present invention. For example, the common 5/6 basic aluminum chloride commercially available as Chlorhydrol has been found not to react with basic zirconium glycinate. Similarly, 2/3 basic aluminum sulfamate does not react with basic zirconium glycinate. Also, if the basic zirconium glycinate or basic zirconium carbonate (described below) is dried down, it will lose its reactivity towards aluminum chloride. However, these examples are more the exception than the rule, and one of ordinary skill in the art can readily determine by routine experimentation whether or not a particular species will be effective within the limits of the present invention.

The acidic or cationic zirconium compounds which may be used in the complexes of the present invention include both the zirconium oxy salts and zirconium hydroxy salts, also referred to as the zirconyl salts and zirconyl hydroxy salts. These compounds may be represented by the following general empirical formula:

$ZrO(OH)_{2-nz}B_z$ wherein Z may vary from about 0.9 to 2 and need not be an integer, n is the valence of B, 2-nz is greater than or equal to 0, and B may be the same as A in the aluminum compounds, that is B may be selected from the group consisting of halide, nitrate, sulfamate, sulfate and mixtures thereof. It will be understood that other Group IV B metals, including hafnium could also be used.

As with the basic aluminum compounds, it will be understood that the above formula is greatly simplified and is intended to represent and include compounds having coordinated and/or bound water in various quantities, as well as polymers, mixtures and complexes of the above. For example, the oxy group in the above general formula could instead be indicated with a water molecule bound to the compound and written as two OH groups. Thus, zirconyl hydroxy chloride could be written as $Zr(OH)_3Cl$ instead of $ZrO(OH)Cl$. Similarly, zirconyl chloride may be written as either $ZrOCl_2$ or $Zr(OH)_2Cl_2$. As will be seen from the above general formula, in which the oxy group is represented as O rather than $(OH)_2$, the zirconium hydroxy salts actually represent a range of compounds having various amounts of the hydroxyl group, varying from about 1.1 to only slightly greater than O groups per molecule.

Particularly preferred zirconium compounds for use in the complexes of the present invention include zirconyl chloride (also referred to as basic zirconium chloride or zirconium oxy chloride) and zirconyl hydroxy chloride, which may be represented by the simple formulas $ZrOCl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g. hydrochloric acid. Other useful zirconium salts will be apparent to those of ordinary skill in the art, such as trioxodizirconium hydroxy halides and similar salts described in U.S. Pat. No. 2,837,400 to Blumenthal, for example.

The zirconium compounds may be incorporated in the complexes of the present invention either alone with the basic zirconium gels or together with the aluminum compounds and/or other metal compounds (such as zinc and magnesium salts) having various antiperspirant effects. However, where the zirconium compounds are incorporated without any aluminum compounds in order to form antiperspirant systems in which zirconium is the only significant active metal, it will usually not be possible to dry the resulting solutions of the complexes to a solid for subsequent reconstitution in water. Of course, the reaction solutions may be used as is. Moreover, such all zirconium systems usually require a stabilizing agent and buffer (see examples below) so that a stable solution of the complex may be prepared having a pH above about 3.

Suitable magnesium compounds for incorporation into the complexes of the present invention include magnesium halides, magnesium sulfate, and magnesium-amino acid salts (such as magensium glycinate), and mixtures thereof. Suitable zinc compounds for incorporation into the complexes of the present invention include zinc halides, zinc sulfate, zinc nitrate, zinc sulfamate, zinc phenolsulfonate and mixtues thereof. Other magnesium and zinc compounds having known antiperspirant advantages will be evident to those of ordinary skill in the art.

The basic zirconium-amino acid compounds of gels useful in preparing the complexes of the present invention may be represented by the following general empirical formula:

$Zr(OH)_z A_{4-z}$ wherein A is an amino acid and $x$ is greater than 0 but less than 4 and need not be an integer. The basic zirconium gels may be characterized by their degree of basicity, depending upon how many hydroxyl groups they contain out of a total theoretical possibility of 4. Thus, for example, one-fourth basic zirconium glycinate refers to the following formula:

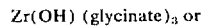
Zr(OH) (glycinate)$_3$ or

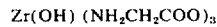
Zr(OH) (NH$_2$CH$_2$COO)$_3$ and one-half basic zirconium glycinate refers to the following formula:

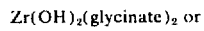
Zr(OH)$_2$(glycinate)$_2$ or

Zr(OH)$_2$ (NH$_2$CH$_2$COO)$_3$

Actually, the above formulas have been greatly simplified for the purposes of clarity. For example, while the gels have been shown as monomers, they are most probably polymeric in form, and may include molecules of water in various coordinated and/or bound forms.

Moreover, due to the unknown nature of the bonds with water molecules, the basic zirconium gels may be shown in either their oxy or hydroxy forms; that is, the oxygens attached to zirconium may be shown as either oxygen alone or hydroxyl equivalents. For example, 3/4 basic zirconium glycinate may be represented by either of the following two formulas:

ZrO(OH) (NH$_2$ CH$_2$ COO)

or

Zr(OH)$_3$ (NH$_2$CH$_2$COO)

Among the amino acids which may be used to form the basic zirconium gels are the so-called neutral amino acids, i.e., amino acids in which the number of amino groups is equal to the number of carboxyl groups in the molecule. Examples of such amino acids include glycine, DL-valine, β-analine, arginine and L-(-)-proline and mixtures thereof. The corresponding basic zirconium gels are the glycinates, DL-valinates, β-alaninates, argininates and L-(-)-prolinates. Other amino acids useful in the present invention will be evident to those of ordinary skill in the art in view of this specification. It is important to note that insoluble derivatives as well as soluble amino acids may be used, in contradistinction to the teachings of U.S. Pat. Nos. 2,814,585 and 2,854,382 to Daley and Grad, respectively, which indicate that only amino acids which are sufficiently soluble in aqueous solution can be used to buffer zirconium antiperspirant solutions.

The basic zirconium-amino acid gels are themselves insoluble in water. However, with moderate heating or stirring, the insoluble basic zirconium gels react with the aluminum antiperspirant compounds to form water soluble antiperspirant complexes. The dissolution of the basic zirconium gels in the aqueous medium is an indiction that a reaction has taken place with the aluminum compound to form a water soluble complex.

It is also important that the gels used in forming the complexes of the present invention be freshly prepared. Thus, it has been found that upon aging for as little as a week or two, the gels begin to lose their capacity to react with acidic aluminum compounds to form antiperspirant complexes. This is manifested by a failure to obtain a clear solution after the reaction process. It is difficult to set a definite time limit for using the gels. However, as used herein "freshly prepared" will be understood to refer to a gel which has been prepared sufficiently recently that a substantially clear solution is obtained when the gel is reacted with an acidic aluminum compound in the appropriate amount.

In general, the relative amounts of the aluminum compound and basic zirconium compound to be reacted together should be such as to yield an Al/Zr mole ratio of between about 10:1 to 1:10, and preferably 3:1 to 1:6. Although relatively high ratios of zirconium are desirable from the standpoint of antiperspirant efficacy, such ratios are sometimes contraindicated due to the greater cost of zirconium. In addition, large amounts of zirconium usually increase the possibilities of skin irritation, but these are greatly mitigated by the buffering action of the hydroxyl and amino acid groups which accompany the zirconium.

In addition to basic zirconium-amino acid gels, basic zirconium carbonate (BZC) gels may also be used to form suitable antiperspirant complexes, by reacting with acidic aluminum halides and lower basic aluminum halides, such as one-third or two-thirds basic aluminum chlorides.

The basic zirconium carbonates may be represented by the following general empirical formula:

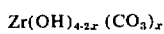
Zr(OH)$_{4-2x}$ (CO$_3$)$_x$ wherein $x$ is greater than 0 but less than 2 and need not be an integer. As with the basic zirconium-amino acid gels, this formula is greatly simplified, and various polymeric and water containing forms are more probable. Also, two OH groups may be represented instead as an equivalent oxide or oxy group. Thus, an example of the above may be represented as Zr(O)CO$_3$ instead of Zr(OH)$_2$CO$_3$. Moreover, it should be understood that these gels may also include bicarbonate groups (HCO$_3$) in addition to or in place of the carbonate groups.

The basic zirconium carbonate gels can be prepared by standard precipitation techniques using sodium carbonate and most any of the usual zirconium oxy or zirconium hydroxy salts previously referred to, such as zirconyl chloride or zirconyl hydroxy chloride. The impurity levels of various undesired ions (e.g. sodium, chloride, etc.) can be controlled in the precipitate by adjusting the pH of the final slurry before filtration and washing.

The acidic aluminum compound and basic zirconium carbonate should be reacted in such proportions as to yield in the final complex an Al/Zr mole ratio of about 4:1 to 1:4, and preferably about 2:1 to 1:2. Such complexes when dissolved in an aqueous solution to the extent of about 5 to 20 weight percent (solids basis) yield a solution pH of at least about 3 and preferably about 3 to 5.

The basic zirconium gels useful in forming the complexes of the present invention also include zirconium hydroxide (Zr(OH)$_4$) gels. It will be observed that these gels are simply the extension of the above general formulas where $x = 4$ in Zr(OH)$_x$ A$_{4-x}$ and $x = 0$ in Zr(OH)$_{4-2x}$ (CO$_3$)$_x$. However, in general due to the higher basicity of the all hydroxide gels, they are less reactive than the amino acid and carbonate analogs, but still react with acidic aluminum solutions.

With the complexes formed with any of the basic zirconium gels, it may be necessary to also include a stabilizing agent or buffer to yield a stable solution and desirable solution pH of at least about 3. Many suitable buffers are known in the art (see for example the Grad and Daley patents referred to above), and others (described in copending applications) have been recently developed. Suitable buffers, which may simply be added to the reaction solution, include urea, amino acids, alkaline and hydroxy salts of amino acids (see copending application Ser. No. 418,712 of Rubino), alkaline earth salts, such as magnesium carbonate, etc. Also, the basic zirconium carbonates can be dissolved first in a glycine solution, for example, to yield water soluble zirconium glycinates. It is preferable that any added buffer be kept to a minimum and preferably less than about 15 weight percent of the complex.

The method of forming the complexes of the present invention is not particularly critical. However, various parameters and properties of the complex such as viscosity and reactivity will be affected by certain variables, including the particular reactants used, the source of the amino acid compound, the order of addition of the reactants and the pH of the final slurry when the product has been precipitated.

The various components are preferably added one at a time, and stirring and/or moderate heating or even refluxing may be advantageous or even necessary to complete reaction of certain ingredients, particularly during and after addition of the insoluble basic zirconium compounds.

Although the basic zirconium compounds may be added as either wet or dry gels, it is greatly preferred to use a wet gel which has never been dried down to a powder form. Thus, it has been found that wel gels are far more reactive with respect to aluminum compounds. That is, drying of the basic zirconium gels appears to reduce the potential reactivity of the gels.

The drying of the finished prepared antiperspirant complexes of the invention is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes a friable solid should be sufficient. If the complex is over dried, so that some of the coordinated and/or bound water is removed, the stability and/or activity of the complex may be interfered with, and the complex may not be readily redissolvable in solvents, particularly hydroalcoholic solvents.

While it has been indicated that the reaction process is not considered particularly critical, it will be understood that sufficient time, heat and agitation are needed to allow reaction of the compounds to form the new complexes of the present invention. This is particularly so in the case of the insoluble basic zirconium compounds used to form complexes of this invention.

As indicated previously, a further feature of the present invention is an improved method for the preparation of the basic zirconium-amino acid gels used in forming the complexes of the present invention. Various zirconium glycinates have been previously reported in the literature. However, these compounds are usually formed by the reaction of zirconyl chloride or zirconyl hydroxy chloride with glycine.

According to the present invention, it has been found that highly reactive basic zirconium-amino acid gels may be formed by reacting in aqueous medium a water soluble salt of an amino acid and a waer soluble zirconium salt, which results in the precipitation of a basic zirconium-amino acid gel.

For example, sodium glycinate may be reacted with zirconyl chloride or zirconyl hydroxy chloride to precipitate out a basic zirconium glycinate (BZG) gel. Only trace impurities will remain in the precipitate since sodium chloride can be readily washed out of the gel.

However, the reaction is not limited to chloride zirconium salts, nor is the amino acid limited to glycine. Instead, virtually any cationic zirconium compounds referred to previously (as extra antiperspirant ingredients) may be used in forming the basic zirconium-amino acid compounds.

The water soluble amino acid salts include particularly the alkali metal salts and ammonium salts of amino acids in which the number of amino groups is equal to the number of carboxyl groups in the acid molecule. Sodium glycinate is particularly preferred of these salts.

The water soluble amino acid salts are preferably prepared by reaction of the alkali metal or ammonium carbonate or bicarbonate with the particular amino acid desired. For example, sodium glycinate is preferably formed by reaction of sodium carbonate or sodium bicarbonate with glycine.

Alternatively, the water soluble amino acid salt could be formed with the corresponding hydroxide instead of carbonate. For example, sodium glycinate could be formed by reacting sodium hydroxide with glycine. However, the amino acid salts formed in this manner are less reactive than those prepared with sodium carbonate. By less reactive is meant reactivity toward active antiperspirant ingredients, such as aluminum chloride, one-third basic aluminum chloride, etc., used in forming the final antiperspirant complexes of the present invention. Although applicants do not wish to be bound by any particular theory, it is believed that the greater reactivity of salts formed from the carbonate or bicarbonate is due to incomplete neutralization with the amino acid. Hence, the final basic zirconium compound will contain carbonate and/or bicarbonate groups, whose presence makes the insoluble zirconium gels more reactive to aluminum.

The preparation of the basic zirconium-amino acid compounds according to the present invention will now be illustrated with reference to the following specific, non-limiting examples:

EXAMPLE A

A sodium glycinate solution was prepared by diluting 336.5 grams of 16° Baume sodium carbonate ($Na_2CO_3$) solution (12% w/w $Na_2CO_3$) with 3 liters of water and dissolving into this solution 52.5 grams of glycine. The above clear solution was titrated into 450 grams of 33% zirconyl hydroxy chloride solution with overhead agitation. The precipitate which formed was filtered and washed. The washed gel analyzed: 5.7% Zr and 0.92% glycine.

EXAMPLE B

A sodium glycinate solution was prepared by diluting 300 grams of 16° Baume sodium carbonate solution with 3 liters of water and then dissolving into this solution 51 grams of glycine. The above clear solution was titrated into 535 grams of zirconyl chloride (5.74% Zr). The precipitate which formed was filtered and washed, and the resulting gel analyzed: 9.1% Zr and 2.7% glycine.

EXAMPLE C

A sodium β-alaninate solution was prepared by diluting 336.5 grams of 16° Baume sodium carbonate with 3 liters of water and dissolving into this solution 62.5 grams of β-analine. The above clear solution was then titrated into 450 grams of 33% zirconyl hydroxy chloride solution with agitation. The precipitate which formed was filtered and washed, and the resulting gel analyzed: 4.37% Zr and 1.2% β-alanine.

The antiperspirant complexes according to the present invention will now be illustraged in more detail, with reference to the following specific, non-limiting examples. Examples I–III illustrate complexes wherein the sodium glycinate was prepared with sodium hydroxide rather than sodium carbonate. As indicated previously, sodium glycinate prepared in this manner is not as reactive with the active antiperspirant ingredients, and hence the glycine content in all of the complexes of these examples is relatively low, namely less than about 1 percent by weight.

Example IV illustrates a preparation using a zirconium hydroxide gel. Sodium carbonate was not used in the preparation of the gel, and the overall reactivity with the basic aluminum and zirconium compounds was correspondingly low.

Examples V–XVI show preparations in which the sodium glycinate or corresponding amino acid salt, used to prepare the basic zirconium-amino acid compound, was prepared from sodium carbonate and the amino acid. The basic zirconium carbonates used in Examples XVII and XVIII were also prepared without the presence of sodium hydroxide.

Except where otherwise indicated, all of the following and foregoing examples were performed in aqueous media, and all percents are on a weight basis.

EXAMPLE I

Forty grams of zirconyl hydroxybromide solution (13.6% Zr) was reacted with 70 g. of 24° Baume $AlCl_3$ solution at 80° C. Into this hot solution was dissolved 20 g. of a basic zirconium glycinate (BZG) gel (4.14% Zr, 1.4% glycine). The above mixture was added slowly to a 25% solution of 5/6 basic aluminum bromide (4.1% Al) while undergoing reflux. The product was oven-dried at 55° C. under a vacuum of 35 cm. of Hg. The material analyzed: 13.2% Al, 7.57% Zr, and 0.84% glycine.

EXAMPLE II

One hundred grams of an aluminum chloride solution (2.1% Al) was heated to 85° C. prior to the addition of 10 g. of a BZG gel (4.74% Zr, 0.91% glycine). After thirty minutes of agitation, the solution cleared. Fifty grams of a 50% solution of aluminum chlorhydrate (5/6 basic aluminum chloride) was added to the cooled solution. The product was oven-dried at 50° C. under a vacuum of 40 cm. of Hg. The material analyzed: 18.0% Al, 1.1% Zr, and 0.46% glycine.

EXAMPLE III

Ten grams of zirconyl chloride solution (14.4% Zr) was mixed in with 40 g. of $AlCl_3$ solution (2.1% Al) and heated to 75° C. prior to reacting with 10 g. of BZG gel (4.14% Zr, 1.4% glycine).

Sixty grams of a 5/6 basic aluminum iodide solution (5.6% Al) was heated to 85° C. prior to the slow addition of the Al-Zr solution described above. On cooling, the pH was 3.6. The product was oven-dried under a vacuum of 38 cm. of Hg at 60° C. The material analyzed: 6.46% Zr, 12.99% Al, and 0.45% glycine.

EXAMPLE IV

Ten grams of a compressed $Zr(OH)_4$ gel (5.1% Zr) was suspended in 90 grams of water to form a 10% suspension containing 0.51% Zr. The suspension was reacted with 2 g. of glycine at 75° C. for one half hour. The slurry was then dissolved in 190 g. of zirconyl hydroxychloride solution (14.1% Zr) plus 20 g. of aluminum chloride solution (4.2% Al) while heating at 85° C. The above was added to 500 g. of aluminum chlorhydrate solution (6.2% Al), which was under reflux. After cooling, 2 g. $ZnCl_2$ and 2 g. $MgCl_2 \cdot 6H_2O$ were dissolved in the solution, to yield a pH of 3.2. The product was oven-dried at 55° C. under a vacuum of 45 cm. of Hg and found to contain: 16.5% Al, 11.8% Zr, 1.01% glycine, 0.37% Zn, and 0.11% Mg.

EXAMPLE V

One hundred grams of aluminum chloride solution (0.84% Al) was heated to 85° C. prior to the addition of 52 g. of a BZG gel (9.1% Zr, 2.7% glycine). After 30 minutes of agitation, the solution cleared, to yield a product with a pH of 3.3. The material was dried in an oven at 55° C. under a vacuum of 45 cm. of Hg, and was found to contain: 35.7% Zr, 5.4% Al and 12.1% glycine.

EXAMPLE VI

Fifty grams of a one-third basic aluminum chloride solution [$Al(OH)Cl_2$; 5.8% Al] was heated to 80° C. prior to the addition of 120 g. of a BZG gel (5.7% Zr, 0.92% glycine). The solution cleared on agitation to yield a solution pH of 3.2. The product was oven-dried at 55° C. under a vacuum of 40 cm. of Hg and was found to contain: 8.98% Al, 16.3% Zr and 3.7% glycine.

EXAMPLE VII

Fifty grams of a 2/3 basic aluminum chloride solution [$Al(OH)_2Cl$; 8.81% Al] was heated to 80° C. prior to the addition of 86 g. of BZG gel (5.7% Zr, 0.92% glycine). After 30 minutes of agitation, the solution cleared to yield a solution pH of 3.1. The product was oven-dried under a vacuum of 40 cm. of Hg at 60° C. The material analyzed: 14.3% Al, 13.5% Zr and 3.14% glycine.

EXAMPLE VIII

Twenty grams of 3/4 basic aluminum bromide solution [$Al_4(OH)_9Br_3$; 9.0% Al] was heated to 80° C. prior to the addition of 15 g. of a BZG gel (5.7% Zr, 0.92% glycine). After 30 minutes of agitation, the solution cleared to yield a solution pH of 3.97. The product was oven-dried at 55° C. under a vacuum of 42 cm. of Hg. The material analyzed: 15.7% Al, 7.2% Zr and 1.71% glycine.

EXAMPLE IX

Thirty-four grams of a BZG gel (5.7% Zr, 0.92% glycine) was dissolved in 40 g. of a zirconyl iodide solution (1.21% Zr). This product was then added to 20 g. of a 25% solution of 5/6 basic aluminum phenolsulfonate (4.2% Al), to yield a product with a pH of 3.85. The solution was evaporated under a vacuum of 45 cm. of Hg at 45° C., and analyzed: 9.2% Al, 19.6% Zr, and 2.63% glycine.

EXAMPLE X

Eighty-six grams of a BZG gel (5.7% Zr, 0.92% glycine) was dissolved 60 g. of a zirconyl nitrate solution [$ZrO(NO_3)_2$; 4.5% Zr]. The above was added to 103 g. of one-third basic aluminum sulfate (3.1% Al). The product was oven-dried at 50° C. under a vacuum of 35 cm. of Hg and was found to contain: ;b 12.4% Al, 26.4% Zr, and 3.14% glycine.

EXAMPLE XI

Fifty-one grams of a BZG gel (4.6% Zr, 0.66% glycine) was dissolved in 40 g. of $AlCl_3$ solution (2.1% Al) which was being heated under reflux. On cooling, the above solution was added to 20 g. of 2/3 basic aluminum sulfamate (4.8% Al). The product was oven-dried at 55° C. under a vacuum of 43 cm. of Hg. The material analyzed: 16.3% Al, 21.3% Zr, and 3.06% glycine.

EXAMPLE XII

Forty grams of a BZG gel (4.6% Zr, 0.66% glycine) was dissolved in 40 g. of $AlCl_3$ solution (2.1% Al) which was being heated under reflux. After the solution cleared, 1 g. of Mg (glycinate)$_2$ (obtained from J. H. Walker and Co.; 13.0% Mg) was added under the same conditions. The resulting clear solution was dried in an oven at 60° C. under a vacuum of 40 cm. of Hg. The product analyzed: 9.33% Al, 20.7% Zr, 1.44% Mg and 2.96% glycine.

EXAMPLE XIII

Forty grams of an aluminum chloride solution (2.1% Al) was heated to 85° C. prior to the addition of 81 g. of BZG gel (4.6% Zr, 0.66% glycine). After 30 minutes of heating with agitation, the solution cleared. Two grams of zinc phenolsulfonate were then dissolved in the cooled solution. The product was oven-dried at 55° C. under a vacuum of 45 cm. of Hg and was found to contain: 5.9% Al, 2.2% Zn and 3.8% glycine.

EXAMPLE XIV

Eighty grams of a zirconyl chloride solution (7.7% Zr) was heated to 80° C. prior to the addition of 108 g. of BZG gel (4.6% Zr, 0.66% glycine). After 15 minutes of agitation, the solution cleared. The cooled solution was then added to 100 g. of a 5% w/w suspension of magnesium glycinate (0.51% Mg. 3.11% glycine) and stirred for 10 minutes until the solution cleared prior to the addition of 12.5 g. of 50% aluminum chlorhydrate (12.5% Al). The product was oven-dried under a vacuum of 45 cm. of Hg at 60° C. The material analyzed: 31.9% Zr, 16.5% Al, 10.6% glycine and 1.38% Mg.

EXAMPLE XV

One hundred five grams of a basic Zr β-alaninate gel (4.37% Zr, 1.2% β-analine) was reacted with 40 g. of refluxing $AlCl_3$ solution (2.1% Al). The mixture was refluxed for one hour when the solution turned clear. On cooling, 2 g. of $ZnCl_2$ and 2 g. of $MgCl_2.6H_2O$ were dissolved in the clear solution. The product was oven-dried at 55° C. under a vacuum of 45 cm. of Hg. The material analyzed: 5.25% Al, 28.6% Zr, 1.5% Mg, 1.18% Zn and 7.9% β-analine.

EXAMPLE XVI

Forty grams of an $AlCl_3$ solution (2.1% Al) was heated to 80° C. prior to dissolving in 105 g. of a basic Zr β-analinate gel (4.3% Zr, 1.2% β-analine). The pH of the solution after cooling was 3.6. The product was oven-dried at 58° C. under a vacuum of 50 cm. of Hg. The material analyzed: 5.8% Al, 19.6% Zr, and 3.3% β-alanine.

EXAMPLE XVII

Five grams of glycine was dissolved in 80 g. of $AlCl_3$ solution (2.1% Al). The solution was heated to 75° C. before dissolving in 90 g. of a basic zirconium carbonate(BZC) gel (7.37% Zr). After 15 minutes of stirring and heating, the solution cleared to yield a pH of 3.52. The product was oven-dried at 60° C. under a vacuum of 45 cm. of Hg. The material analyzed: 5.24% Al, 19.3% Zr and 13.3% glycine.

EXAMPLE XVIII

Thirty-six grams of a basic zirconium carbonate (BZC) gel (5.67%) was dissolved in 40 g. of refluxing $AlCl_3$ solution (2.1% Al). The cooled solution had a pH of 3.2. The product was oven-dried at 60° C. under a vacuum of 40 cm. of Hg. The material analyzed: 7.19% Al, 19.6% Zr.

Among the advantages of the complexes of the present invention is that highly acidic aluminum or aluminum-zironcium antiperspirant systems may be effectively buffered with a complex which also provides an additional source of zirconium, a metal which is known for its antiperspirant efficacy. Moreover, due to the presence of the additional basicity (hydroxyl groups) in the buffering complex, smaller amounts of amino acid are required in the final complex than have been required in many prior art antiperspirant systems using amino acids as buffers.

As indicated previously, the complexes of the present invention may be used in a variety of conventional antiperspirant forms which are applied to the human axilla for effective perspiration inhibition. In such formulations, the complex should be present in amounts of about 1.5 to 20 weight percent (depending on the type of formulation employed).

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic mixed solvents, such as 50 percent ethanol and 50 percent water. In either the aqueous solutions or the hydro-alcoholic solvents, the complexes of the present invention should be present in the above antiperspirant forms in amounts of about 5 to 20 weight percent of the active ingredient (calculated on a solids basis).

The complexes of the present invention may also be used in the now popular powder-in-oil aerosol sprays. The powder-in-oil systems comprise the dispersion of a finely divided antiperspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical antiperspirant formulations employing the complexes of the present invention are exemplified in Table I.

SAMPLE R

A 10 weight percent aqueous solution of Chlorhydrol (5/6 basic aluminum chloride) was used as the standard or reference solution.

SAMPLE E

A complex according to the present invention was prepared by reacting 52 grams of a basic zirconium glycinate gel (9.1% Zr, 2.5% glycine) with 40 grams of $AlCl_3$ solution (2% Al). The mixture was refluxed at 80° C. until the solution cleared. The resulting solution had a pH of 3.1. The material was dried in an oven at 50° C. under a vacuum of 45 cm of Hg. The product assayed 4.2% Al, 28.2% Zr and 11.0% glycine (Al/Zr ratio = 0.5:1). A 10% w/w aqueous solution was prepared for testing by dissolving 20 grams of the product in 180 grams of water. The clear solution had a pH of 3.5.

TABLE I

ANTIPERSPIRANT FORMULATIONS

| Ingredient | A*<br>Powder<br>-in-oil<br>aerosol | B*<br>Powder<br>-in-oil<br>extra-dry<br>aerosol | C<br>Spray:<br>(Manual<br>-Pump) | D<br>Oil-in-<br>water<br>lotion | E<br>Oil-in-<br>water<br>cream |
|---|---|---|---|---|---|
| Active Ingredient | | | | | |
| (Antiperspirant) | | | | | |
| Complex of Example I | 3.5 | | | | |
| Complex of Example II | | | 10.0 | | |
| Complex of Example IV | | 5.0 | | | |
| Complex of Example VIII | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane) | 45.0 | 45.0 | | | |
| Water | | | 19.5 | 66.0 | 56.0 |
| Alcohol SD-39C | | | 55.0 | | |
| Talc, U.S.P. | | 1.5 | | | |
| Arlacel 165 (4) | | | | | 18.0 |
| Amerchol L-101 (2) | | | | 5.0 | |
| Solulan 98 (2) | | | | 2.0 | |
| Myrj 52 (4) | | | | 4.0 | |
| Cetyl Alcohol | | | | 2.0 | |
| Glycerin | | | | 2.0 | 5.0 |
| Veegum HV (3) | | | | 1.0 | |
| Preservative | | | | q.s. | q.s. |
| Spermaceti | | | | | 5.0 |
| Titanium Dioxide | | | | | 1.0 |

(1) Cab-O-Sil M-5 - fumed amorphous silica of Cabot Corp.
(2) Amerchol L-101 and Solulan 98 - lanolin derivatives of Amerchol, Inc.
(3) Veegum HV - product of R. T. Vanderbilt & Co.
(4) Arlacel 165 and Myrj 52 - non-ionic emulsifiers of ICI America, Atlas Chem., Div.
*For "powder-in-oil" aerosols, active ingredient powders are ground before use in a micronizer to yield powders containing a particle size greater than 97% through a 325 mesh screen (44u).

In order to test the antiperspirant efficacy of the complexes of the present invention, several aqueous antiperspirant solutions, including ones made according to the present invention, were tested by an independant testing laboratory. The testing procedure was similar to that described in detail in copending application Ser. No. 41,995 of Rubino for "Basic Magnesium-Aluminum Compositions Useful As Antiperspirants".

Three complex solutions according to the presnet invention were each tested against a basic aluminum chloride solution as a standard or reference. The test samples were as follows:

SAMPLE I

A complex according to the present invention was prepared by reacting 145 grams of basic zirconium carbonate gel (4.95% Zr) with 200 grams of $AlCl_3$ solution (2.1% Al). The mixture was refluxed at 80° C. until the solution cleared. To the cooled solution was added 3 grams of glycine. The resulting clear solution had a pH of 3.3. The material was dried in an oven at 50° C. under a vacuum of 45 cm of Hg. The product assayed 35.1% Zr, 21.1% Al and 15.0% glycine (Al/Zr ratio = 2:1). A 10% w/w aqueous solution was prepared for testing by dissolving 20 grams of the product in 180 grams of water. The clear solution had a pH of 3.2.

Sample L

A complex according to the present invention was prepared by reacting 100 grams of basic zirconium carbonate gel (6.21% Zr) with 120 grams of 11.1% zirconyl hydroxychloride solution (4.8% Zr). The mixture was refluxed at 80° C. until the solution cleared. One gram of glycine was dissolved in the cooled solution. The solution assayed 3.5% Zr, 0.3% glycine and 0.6% Cl (Zr/Cl ratio = 2.2:1). The solution was used as is for testing.

Each of the above samples according to the present invention was tested against the standard or reference solution using groups of women (13 per group) from the Miamiville, Ohio area. The study was carried out in five one week periods, with a two-week rest period between the test weeks. During the first week, each group of 13 women was tested with reference solution, and during each of the remaining four test weeks, the groups were tested with one of four other antiperspirant solutions, which included among them the above samples according to the present invention.

The test solutions were applied by means of cotton swabs in 0.5 ml portions. During the first test week, four separate applications of the reference solution were made, and in each of subsequent test weeks five separate applications of one of the other four solutions were made. Sweat collection were made before the first application as a control, 22 hours after the last application, and 1 hour after each of the other applications.

The average percentages of sweat reduction, together with the calculated 95% confidence limits, are given below:

| Sample | % Sweat Inhibition | | | Means of 1 hr. collections | 22 hrs. after last appl'n |
|---|---|---|---|---|---|
| | 1 hr. after appl'n No. 2 | 1 hr. after appl'n No. 3 | 1 hr. after appl'n No. 4 | | |
| | Group II | | | | |
| R | 26.3 ± 9.8 | 33.8 ± 10.4 | — | 30.0 ± 8.6 | 27.8 ± 10.0 |
| E | 42.7 ± 7.8 | 50.2 ± 8.6 | 45.1 ± 8.8 | 45.7 ± 8.0 | 45.2 ± 9.0 |
| | Group III | | | | |
| R | 28.5 ± 9.4 | 33.9 ± 8.4 | — | 31.2 ± 7.4 | 30.0 ± 10.4 |
| I | 45.4 ± 9.6 | 42.9 ± 12.4 | 49.1 ± 11.2 | 46.8 ± 9.4 | 47.6 ± 9.6 |
| L | 34.9 ± 13.0 | 42.4 ± 8.0 | 37.2 ± 10.4 | 38.1 ± 9.8 | 34.3 ± 8.6 |

A demonstrated sweat inhibition of more than about 20 percent on a repeated application is regarded as substantially effective. The measurement usually considered most important is the one taken 22 hours after the last application. It is significant that the complex solutions of the present invention tested above showed improved antiperspirant efficacy over the 10 percent basic aluminum chloride solutions used as the reference. There was no evidence of axiallary irritation during any of the tests.

The present invention may be embodied in other specific forms without departing from the spirit or essential attributes thereof and, accordingly, reference should be made to the appended claims, rather than to the foregoing specification as indicating the scope of the invention.

We claim:
1. A process for making a water soluble, astringent aluminum-zirconium complex comprising reacting:
 a. an aluminum compound selected from the group consisting of aluminum halide, basic aluminum halide, basic aluminum sulfate, basic aluminum nitrate, basic aluminum sulfamate, basic aluminum phenolsulfonate, and mixtures thereof; and
 b. a freshly prepared basic zirconium compound comprising a basic zirconium-amino acid gel, said compounds being added in such amounts as to yield in the complex an Al/Zr mole ratio of about 10:1 to 1:10.
2. A process according to claim 1 wherein said compounds are reacted in aqueous medium to yield an aqueous solution containing about 5 to 20 weight percent (solids basis) of said complex, and the pH of said solution is at least about 3.
3. A process according to claim 1 wherein said freshly prepared basic zirconium-amino acid gel has the general empirical formula:

$$Zr(OH)_x A_{4-x}$$

wherein A is an amino acid and $x$ is greater than 0 and less than 4 and need not be an integer.
4. A process according to claim 3 wherein $x$ is about 2 to 3.5.
5. A process according to claim 3 wherein the amino acid is selected from the group consisting of glycine, DL-valine, β-alanine, arginine, L-(-)-proline, and mixtures thereof, and the amino acid comprises greater than one percent by weight of the total complex formed.
6. A process according to claim 1 wherein a buffer is also added to maintain the pH of a 5 to 20 weight percent aqueous solution of the complex at at least about 3.
7. A process according to claim 3 wherein the basic zirconium-amino acid gel is precipitated from the reaction of a water soluble salt of the amino acid with a water soluble zirconium oxy or zirconium hydroxy salt.
8. A process according to claim 1 which also includes reacting a zirconium compound selected from the group consisting of zirconium oxy salts, zirconium hydroxy salts, trioxodizirconyl hydroxy salts, and mixtures thereof.
9. A process according to claim 1 which also includes reacting a magnesium compound selected from the group consisting of megnesium halide, magnesium sulfate, magnesium-amino acid salts, and mixtures thereof.
10. A process according to claim 1 which also includes reacting a zinc compound selected from the group consisting of zinc halide, zinc sulfate, zinc nitrate, zinc phenolsulfonate, zinc sulfamate, and mixtures thereof.
11. A process according to claim 1 wherein said basic zirconium-amino acid gel is a wet gel.
12. A process for making a water soluble, astringent aluminum-zirconium complex comprising reacting:

a. an aluminum compound selected from the group consisting of aluminum halide, lower basic aluminum halide, and mixtures thereof,
b. a basic zirconium carbonate gel, and
c. an amino acid, said compound and said gel being added in such amounts as to yield in the complex an Al/Zr mole ratio of about 4:1 to 1:4.

13. A process for making a water soluble, astringent zirconium complex comprising reacting in aqueous solution:
    a. a zirconium compound selected from the group consisting of zirconium oxy salts, zirconium hydroxy salts, trioxodizirconyl hydroxy salts, and mixtures thereof;
    b. a freshly prepared basic zirconium compound comprising a basic zirconium-amino acid gel; and
    c. a buffer such that a stable solution containing five to twenty weight percent of the complex will have a pH above about 3.

14. A process according to claim 13 wherein said buffer is selected from the group consisting of urea, amino acids, alkaline and hydroxy salts of amino acids, and alkaline earth salts.

* * * * *